(12) United States Patent
Wolf et al.

(10) Patent No.: US 7,681,449 B2
(45) Date of Patent: Mar. 23, 2010

(54) METAL LOSS RATE SENSOR AND MEASUREMENT USING A MECHANICAL OSCILLATOR

(75) Inventors: Henry Alan Wolf, Morristown, NJ (US); Manuel S. Alvarez, Warrenton, VA (US); James E. Feather, Burke, VA (US); Philip J. Cacciatore, Manassas, VA (US); Jason B. English, Roswell, NM (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 424 days.

(21) Appl. No.: 11/710,657

(22) Filed: Feb. 23, 2007

(65) Prior Publication Data

US 2007/0199379 A1    Aug. 30, 2007

Related U.S. Application Data

(60) Provisional application No. 60/777,491, filed on Feb. 28, 2006.

(51) Int. Cl.
  *G01N 17/04* (2006.01)
(52) U.S. Cl. .................... 73/579; 73/24.01; 73/64.53
(58) Field of Classification Search ............ 73/579, 73/590, 580, 24.01, 64.53
  See application file for complete search history.

(56) References Cited

U.S. PATENT DOCUMENTS

| | | | | |
|---|---|---|---|---|
| 3,056,284 A | * | 10/1962 | Marsh et al. ............... | 73/597 |
| 3,253,219 A | * | 5/1966 | Littler ...................... | 324/71.1 |
| 4,788,466 A | * | 11/1988 | Paul et al. ............... | 310/323.06 |
| 5,208,162 A | * | 5/1993 | Osborne et al. ............. | 436/6 |
| 5,571,944 A | * | 11/1996 | Pfeifer et al. .............. | 73/24.04 |
| 5,719,324 A | * | 2/1998 | Thundat et al. ............ | 73/24.01 |
| 5,734,098 A | * | 3/1998 | Kraus et al. ............... | 73/61.62 |
| 6,389,891 B1 | | 5/2002 | D'Angelico et al. | |
| 6,639,402 B2 | * | 10/2003 | Grimes et al. ............. | 324/239 |
| 6,928,877 B2 | | 8/2005 | Carlson et al. | |
| 7,148,611 B1 | * | 12/2006 | Liu .......................... | 310/366 |
| 7,204,128 B1 | * | 4/2007 | Liu et al. .................. | 73/53.01 |
| 2002/0178787 A1 | * | 12/2002 | Matsiev et al. ............ | 73/24.01 |
| 2004/0197227 A1 | * | 10/2004 | Hauan et al. ............... | 422/58 |
| 2006/0037399 A1 | | 2/2006 | Brown | |
| 2008/0314150 A1 | * | 12/2008 | Wolf et al. ................... | 73/579 |

FOREIGN PATENT DOCUMENTS

| | | | | |
|---|---|---|---|---|
| JP | 07225184 A | * | 8/1995 | |
| JP | 08193937 A | * | 7/1996 | |
| JP | 2003240703 A | * | 8/2003 | |
| JP | 2003315254 A | * | 11/2003 | |
| JP | 2004340766 A | * | 12/2004 | |

* cited by examiner

*Primary Examiner*—Hezron Williams
*Assistant Examiner*—Rose M Miller

(57) ABSTRACT

The present invention is a mechanical oscillator metal loss sensor for use in a corrosive or erosive environment. The elements include a mechanical oscillator that is mechanical excited with two regions that corrode differently, where the regions are determined to affect specific influences on the resonance parameters, wherein said mechanical oscillator has a resonant frequency, f, and a quality factor, Q. In a preferred embodiment, the mechanical oscillator has the shape of a tuning fork.

37 Claims, 11 Drawing Sheets

Distinguishes Deposition and Mass Loss as a Function of Position on Tine for Fork A Frequency response at base to metal loss and epoxy deposition plotted on the same axis Corrosion Measurement Using a Reference Fork Frequency Change to Mass Loss by Two Similar but Not Identical Tuning Fork Oscillators Components of Commercial Tuning Fork Level Sensor (Fork A)

Components of Commercial Tuning Fork Level Sensor (Fork B)

Distinguishes Deposition and Mass Loss as a Function of Position on Tine for Fork A Frequency response at base to metal loss and epoxy deposition plotted on the same axis Deposition over the entire fork tine and Mass Loss as a Function of Position on Tine for Fork B

- Metal loss = H($\Delta$f steel loss)

Figure 6
Effect on Q and Resonance Frequency of Deposition on Tines and Diaphragm (Fork B with a metal mass loss = 0.250g))

a. Relative effect of resonance frequency and Q as a function of wax deposition
Arrows show approach used in the example for estimating the impact of frequency shift of deposition using the parameter Q.

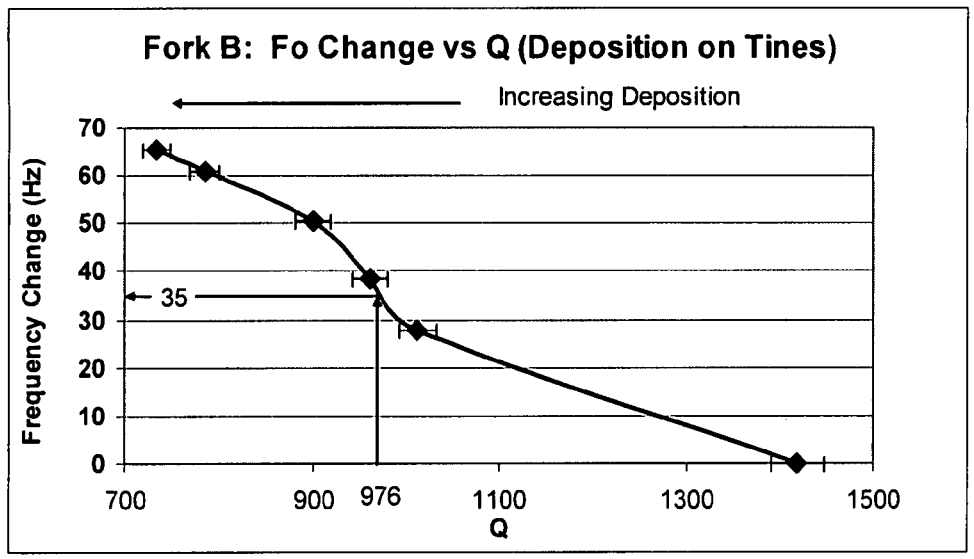

b. Absolute effect on frequency with respect to deposition

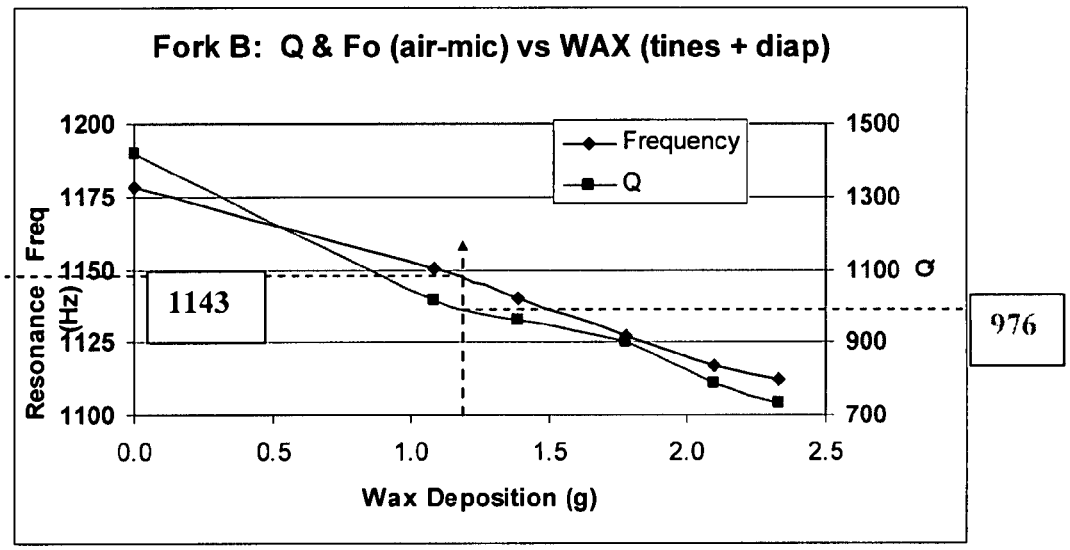

Figure 7
Change in Q From Metal Mass Loss at the Tine Base (FORKS A and B)
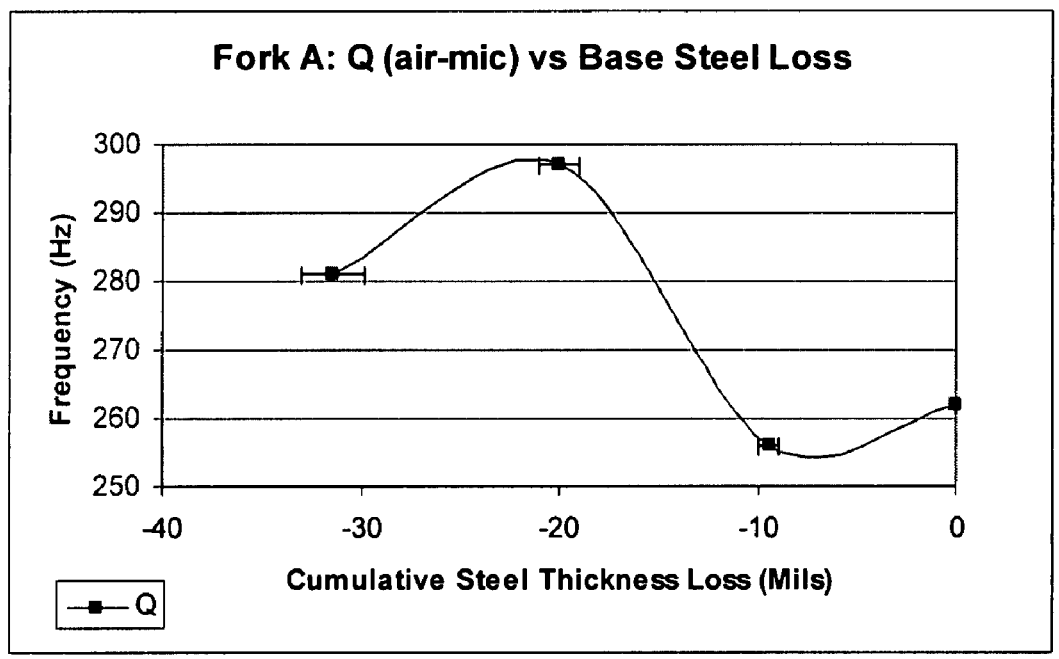
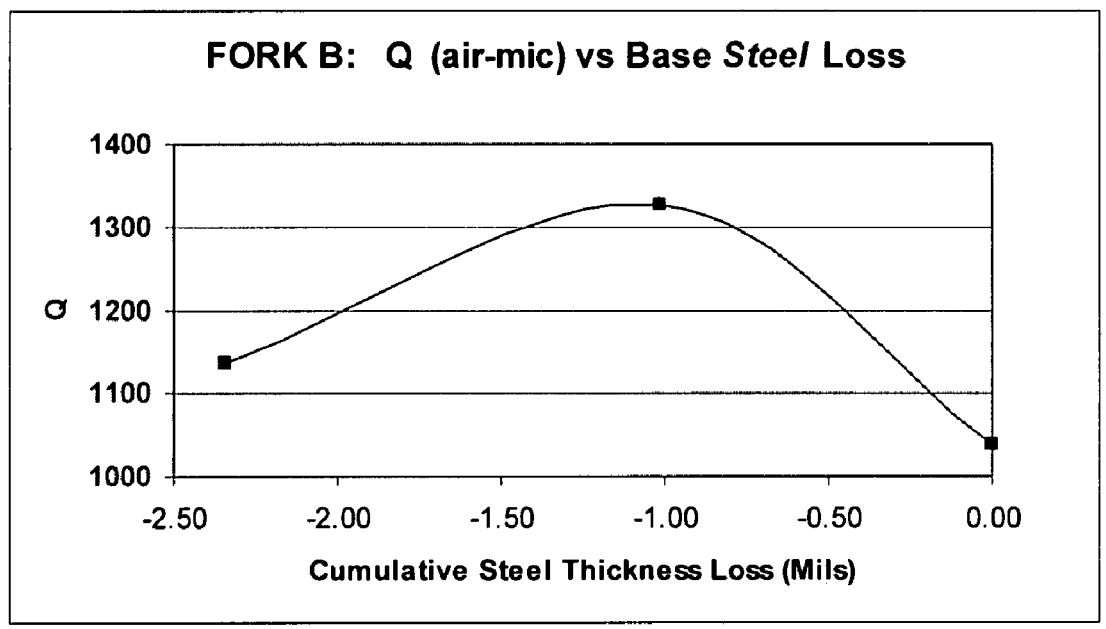

Comparison between Experimental and FEA Results

Corrosion Rate of Carbon Metal as a Function of Impact Angle

Tuning Fork Oscillator Resonance Frequency as a Function of Temperature

Example Where Corrosive Fluid Addition Has No Impact on Resonance Frequency

Example Where Corrosive Fluid Has Impact o n Resonance Frequency

Application of Finite Element Analysis (FEA) Optimize the Paddle Shape by
Minimizing the Effect of Deposition Material

METAL LOSS RATE SENSOR AND MEASUREMENT USING A MECHANICAL OSCILLATOR

This application claims the benefit of U.S. Provisional Application 60/777,491 filed Feb. 28, 2006.

BACKGROUND OF THE INVENTION

The present invention relates to a metal loss measurement system for the detection of corrosion and for measuring the rate of metal mass loss. The invention may be applied generally to the detection of metal-loss by corrosion and/or erosion species in single or multiphase fluids. In particular, the present invention relates to the on-stream detection of metal-loss corrosion and/or erosion during an industrial production process. The actual service environment may be aqueous, hydrocarbon, chemical or a combination.

Corrosive species involved in the production and processing of crude oil and hydrocarbons may cause metal-loss corrosion of production, transfer, storage, and processing equipment. Erosive species typically involve fluid and/or solids turbulence causing metal loss from mechanical actions rather than chemical. For example, these corrosive/erosive species may be hydrocarbon, hydrocarbon containing materials, or aqueous, or combinations thereof. Moreover, streams may be single or multi-phase (solids, liquids, gases).

High performance, relatively low-cost corrosion (erosion) sensing technology as in the instant invention would enable, for example, optimization utilization of corrosive crudes and corrosion inhibitor additions, and reductions in unplanned capacity loss, turnaround time, and inspection costs due to corrosion-induced equipment failures. Additional value is achievable with the application of the instant invention to corrosion monitoring of transfer, process, and storage equipment used for crude oil, fractions and derived products, and chemicals and other industries concerned with corrosion and erosion. Further value is achievable with the application to monitoring metal-loss corrosion in equipment used for the extraction of crude oil from subsurface and subsea deposits. In these and other services, a by-product of the corrosion is scale or other depositions that are adherent to the containment surface. A feature of the instant invention is that the metal loss measurement is not compromised by these non-metallic depositions.

Current corrosion sensing technologies, for example electrical resistance probes, fall far short of the performance level required to achieve the economic incentives described above. Their shortcomings are that: One limitation relates to sensitivity versus useful sensor life. Increasing sensitivity of the conventional electrical resistance probe is achieved by decreasing the thickness of the sensing element. However, the decrease in thickness results in a reduced life of the probe. Once corrosion results in a breach of the element, the probe will no longer function and must be replaced. In an operating process unit, on-stream probe replacement poses various safety and hazard issues. Another limitation of the electrical resistance probes relates to their inherent signal variability. The signal variability caused by thermal changes and other factors that affect electrical resistance necessitate long data collection periods (often a week or longer) to establish a reliable trend. While conventional electrical resistance probes are based on understood theoretical principals, these probes often provide low reliability and poor sensitivity to corrosion rates due to limitations in their design and manufacture. The typical output is often difficult for estimating a quantitative corrosion rate.

It is well established in the literature (references 3 and 4) that the lightly damped harmonic oscillator with single degree of freedom can be mathematically expressed by a second order differential equation. If the forcing function is sinusoidal, the resonance frequency and quality factor, Q, can be represented by:

$$fo=(1/2\pi)\sqrt{(k/m)}$$

$$Q=(1/c)*\sqrt{(k*m)}$$

Where
m=system mass
k=system stiffness
c=velocity dependent damping
fo=resonance frequency
Q=Quality factor (a measure of the system damping and energy dissipation)

There is an implicit assumption that the damping is light so that the mechanical resonance can be observed.

U.S. Pat. No. 6,928,877 and US application 2006/0037399 both employ resonators and teach a relationship between the resonance frequency and mass change. The relationship taught by the prior art is consistent with the well-known solution described above for a single degree of freedom lightly damped mechanical oscillator: a mass decrease will result in a frequency increase and a mass increase will result in a frequency decrease. The instant invention teaches away from the prior art by discovering and utilizing that mass decrease from corrosion/erosion can also result in a resonance frequency decrease. Clearly this finding is not obvious in light of the teachings of the prior art. However, this finding is actually consistent with the governing equations previously listed. The instant invention has utilized that the stiffness of the resonator device is also governed by the system mass. Moreover, that relationship between system mass and stiffness is location dependent: the amount of change to the system stiffness is dependent upon where the mass is lost (or gained). The instant invention teaches that by selecting the proper location on the vibrating element, it is possible that the change in the stiffness to mass ratio of equation (1) can be stiffness dominated even though mass is being lost. For that case, a loss of mass will result in a frequency decrease, teaching away from the prior art.

U.S. Pat. No. 6,928,877 also teaches to make the mass additions or losses at the tip of the resonator. The instant invention teaches away from making the tip the mass change location. In fact, the instant invention provides details for minimizing any mass change at the resonator tip. For the instant invention, the resonator's mass change location is designed to be close to tine the attachment point. At this location, mass loss has a sufficient impact on system stiffness as to cause a resonance frequency decrease. Essentially, mass change at this location on the tuning fork resonator is controlling the system resonance frequency because of the corresponding change to stiffness. Moreover, mass addition from corrosion scale or fouling near the base has minimal impact on the resonance frequency because scale and fouling do not significantly contribute to system stiffness. This observation is understood because the Young's modulus (a measure of a material's stiffness) of scale or fouling is several orders of magnitude lower than steel. However, if scale or fouling deposition were to occur near the resonator tip, the added mass would result in a frequency decrease. Any change to the system stiffness is overshadowed by the mass change.

US application 2006/0037399 also teaches away from employing stiffness changes to the resonator inherent mass by the use of installing corrodible material in pockets. That application describes the use of pockets to facilitate the periodic replacement of corrodible elements installed in the pockets. The ability to employ the device stiffness of the instant invention is dependent upon the corrodible element being an integral element of the resonator (e.g. attached securely via welding). Corrodible elements attached by means of pockets in US application 2006/0037399 would not meet the criteria enabling a stiffness change to the resonator. Attachment via pockets can only enable a mass change.

U.S. Pat. No. 6,928,877 does not consider the situation of simultaneous metal mass loss and fouling deposition. US application 2006/0037399 teaches that mass loss will increase the resonance frequency and that fouling deposition will decrease the resonance Q. Therefore, 2006/0037399 teaches that the fouling condition in the presence of mass loss (corrosion or erosion) can be recognized by the Q measurement. The application teaches that a neural network or artificial intelligence can be used to infer corrosion and fouling conditions from the resonance parameters. The instant invention teaches away from these empirical and unreliable approaches by designing a probe where the resonance frequency is primarily dependent upon corrosion (steel) mass loss and is substantially insensitive to deposition from fouling or corrosion products.

The focus of U.S. Pat. No. 6,928,877 and 2006/0037399 is to provide a quantitative estimate of mass loss or deposition. Essentially, both provide an alarming function. The instant invention has sufficient precision, stability, and longevity as to provide a mass loss rate quantity.

SUMMARY OF THE INVENTION

The present invention is a corrosion/erosion sensor and a method for its use in a corrosive liquid or gas environment. The invention uses the changes in the resonance parameters of a mechanical oscillator to determine the metal mass loss of the oscillator. However, several corrosion mechanisms also result in scale deposition. Since the desired result is metal mass loss, the effects of scale deposition should be considered. An example of corrosion scale in refining processes is iron sulfide: formed by the iron removal from the pressure containment boundary reacting with various sulfur species in the process fluids. In addition, some processes are fouling resulting in deposits such as coke, inorganic salts, or wax. Ammonium chloride is an example of a salt deposition that occurs in various aqueous containing streams in the processing of crude oils. Coking can occur when the temperature of the metal surface is higher than the temperature of the service fluid. The present invention determines metal loss, including loss from, corrosion employing a mechanical design that minimizes the interference from deposition.

The sensor consists of a mechanical oscillator. In the most general embodiment, the oscillator has a vibrating element such as tuning fork tines or a rod. As examples, the cross-sectional shape of the tines or rod may be circular, rectangular, or as otherwise determined by finite element analysis described subsequently. These vibrating elements are attached to a diaphragm. The vibrating elements (e.g. tines or rod) have regions that respond to the service fluid at different corrosion rates. The vibrating element includes a base and a tip region. The oscillator has a resonance frequency, f, and the quality factor associated with the resonance, Q. The resonance factor Q is inversely proportional to the total system damping. The mechanical excitation may be provided by the flow of the service fluid or by active excitation at the diaphragm. As an example, this active excitation may be provided by a piezoceramic driver. When driven by an external energy source, such as a piezoceramic driver, it is not required to continuously provide the excitation. The excitation can be applied at the times it is desired to interrogate the corrosion sensor.

In one embodiment, a single tuning fork with two regions of differing corrosion resistance is used. Regions of differing corrosion resistance include the case where one of the regions does not corrode at all. In a preferred embodiment, both regions are subjected simultaneously to the corrosive environment. In another embodiment, a second non-corrodible tuning fork is used as a reference fork. In both embodiments, both resonance frequency and Q are available in the determination of metal mass loss and scale/fouling deposition. In the dual sensor embodiment, the second fork is used to track process fluid changes such as viscosity, density and temperature not attributed to corrosion. In the special case that uses a reference oscillator and where the corrodible oscillator is constructed to minimize the frequency change caused by corrosion scale deposition, it is sufficient to use resonance frequency to determine metal loss, In the single fork embodiment, the temperature-related changes are accounted for using a thermocouple, where viscosity and density changes take place as a function of temperature for a fixed composition. Changes caused by depositions are addressed using the Q parameter.

BRIEF DESCRIPTION OF THE DRAWINGS

FIG. 6a shows the effect on Q and relative change in frequency, f, of deposition on tines and diaphragm for fork, B with metal mass loss equal to 0.25 g. FIG. 6b shows the absolute effect of resonance frequency and Q with respect to deposition.

FIG. 7 shows the change in Q from mass loss at the tine base for forks A and B.

DETAILED DESCRIPTION OF THE PREFERRED EMBODIMENTS

Figure 1A:
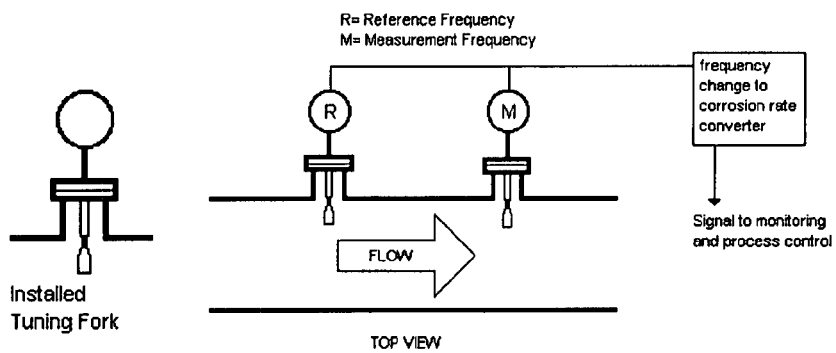
FIG. 1a shows a schematic drawing of a dual tuning fork embodiment of the present invention.

This invention represents a new application of existing commercial technology. The existing commercial applications include the on-line in-situ measurement of fluid level, density and/or viscosity of process streams in a wide range of industries. The invention involves the measurement of changes in the resonant parameters (frequency, Q) of a tuning fork immersed in a process stream to detect metal loss. The current commercially available devices use these parameters to determine the density and the viscosity of the medium. The underlying assumption in these devices for measuring fluid level, density and/or viscosity is that the mass of the oscillator is fixed and its mechanical properties are fixed at the operating temperature. Another assumption is that there is no mass deposition on the tuning fork by the service fluid. Some commercial systems available include a temperature measurement to compensate for changes in mechanical properties. Moreover, in these commercial systems, the material used for the oscillator is compatible (e.g. non-corrosive) with the process fluid in the intended application.

The present invention uses the changes in the tuning fork resonance parameters caused by a corrosion/erosion mass loss. However, a complication arises in that several corrosion mechanisms also result in scale deposition or may be accompanied by fouling deposition. Since the desired result is to measure metal mass loss, the effects of these depositions should be considered. Several distinct embodiments have been developed to address these issues.

In one embodiment, a device would be constructed which employs two mechanical oscillators. One oscillator would be made of a material totally compatible (non-corrodible) with the process fluid (for example stainless steel or other high alloy material known to be fully compatible with the service), and the other oscillator would include some materials that can corrode. Preferably, this corroding material would be of the same composition as the service pressure boundary (e.g. pipe or pressure vessel). This approach of using two oscillators can be used to minimize effects of corrosion scale or fouling deposition as well as changes associated with process density, viscosity, temperature.

In another embodiment, a single mechanical oscillator is used to fabricate the metal loss probe sensor. Using a single oscillator, the following characteristics can be used to enhance the corrosion probe performance: a) shape (e.g. rod, especially shape-configured tines); b) two regions (e.g. tip and base) with differing corrosion responses (achieved using a bimetallic construction or a single metallic construction employing a corrosion resistant coating (either metallic or non-metallic); d) signal processing (Q and f). Collectively, this configuration and these parameters are sufficient to measure corrosion accounting for both forms of deposition: corrosion scale and fouling. The concurrent measurement of temperature can be used to account for small changes in the temperature, density, viscosity of the service fluid that may have a corresponding affect on the resonance parameters (Q and f).

Embodiment Using A Reference Oscillator (e.g. Multiple Oscillators)

The fully compatible mechanical oscillator (non-corrodible) is used as a reference measurement, and it would be used to track process fluid changes (such as viscosity, density and temperature) that would influence the observed changes in the oscillator not attributable to corrosion (FIG. 1a). The second oscillator (with a portion of the material being affected by the process fluid, as in the case of corrosion) experiences the same changes, but in addition it would experience the changes due to the corrosion caused by the fluid. This difference in behavior is then translated into a metal loss rate for the material at the process conditions, and is used to monitor the corrosion/erosion rate to determine safe operation, effectiveness of corrosion inhibitors, inhibitor dosage control and/or predicting remaining wall in piping and vessels. Other embodiments are also possible and described. To minimize the impact of corrosion scale deposition, the corrodible oscillator can be configured using elements with different corrosion rates as describe in the single oscillator embodiment.

This embodiment of using two oscillators can be used to account for the effects of corrosion scale or fouling deposition. The approach also has the benefit of directly accounting for minor variations in the service fluid impacting temperature, density, and viscosity. In the absence of any corrosion, the change in resonance parameters (Q and frequency) of both oscillators can be directly attributable to parameters other than mass loss (e.g. deposition, density, etc.). Any divergence between the resonance parameters of the two oscillators is attributable to mass loss in the oscillator fabricated with the corrodible components. If the two oscillator approach is to be deployed, the effects of corrosion scale deposition can be minimized using the oscillator design using multiple corrodible elements described in the preferred embodiments. There are two reasons the multiple tuning fork approach may be less desirable than the single oscillator approach of the preferred embodiments. One reason is the cost of materials and installation of the second oscillator. The other reason is the assumption that both oscillators will be exposed to the same corrosion and process environments.

Figure 1B:
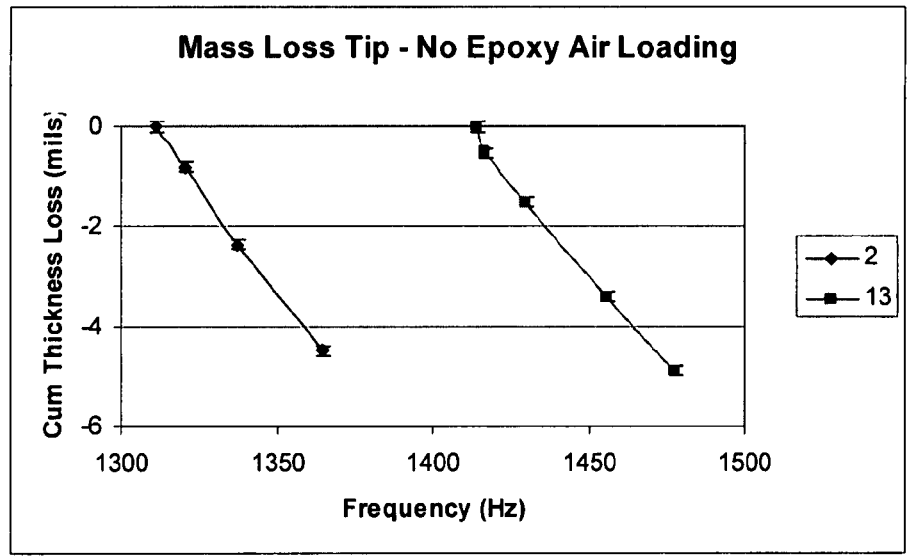
FIG. 1b shows the frequency change to mass loss by two similar but not identical tuning forks.

There are fundamental principles associated with the two oscillator system. The first principle is that the two oscillators are closely positioned so that changes in process conditions (composition, density, fouling, etc.) impact both oscillators in the same manner. The second principle is that both oscillators respond to these changes in a predicable manner. The third principle is that corrodible oscillator is constructed in accord with guidelines of this invention to minimize the effects of deposition of the corrosion product. In general, the two oscillators would have similar resonance characteristics (frequency, Q, amplitude, harmonics). Then a suitable compensation algorithm is determined for oscillators having unmatched parameters. An algorithm is established by measurement using non-identical oscillators with similar resonance characteristics. An example of tuning fork oscillators with similar but not identical resonance frequency response is shown in FIG. 1b. In this example, the oscillators do respond to changes in a predictable but not identical manner. Using two forks, it is not only necessary to monitor the changes as they occur in the corroding fork but it is also necessary to compare those data with changes in the reference fork. If the third principle identified above is applied, then it is sufficient to track frequency changes to measure metal loss. If the third principle is not applied, then changes in frequency and Q should be monitored.

Metal thickness loss and deposition gains shown in the examples in this invention represent the single-sided loss or gain. The actual metal loss or deposition gain was achieved uniformly over the tuning fork tine. However, it is reported herein as the single-sided result to be consistent with the metal loss (or scale deposition) as it would occur on the interior of the pressure containment boundary (typically the interior of a pipe or a vessel).

DETAILED DESCRIPTION OF THE PREFERRED EMBODIMENTS USING A SINGLE FORK MECHANICAL OSCILLATOR CORROSION/EROSION PROBE

Figure 2:
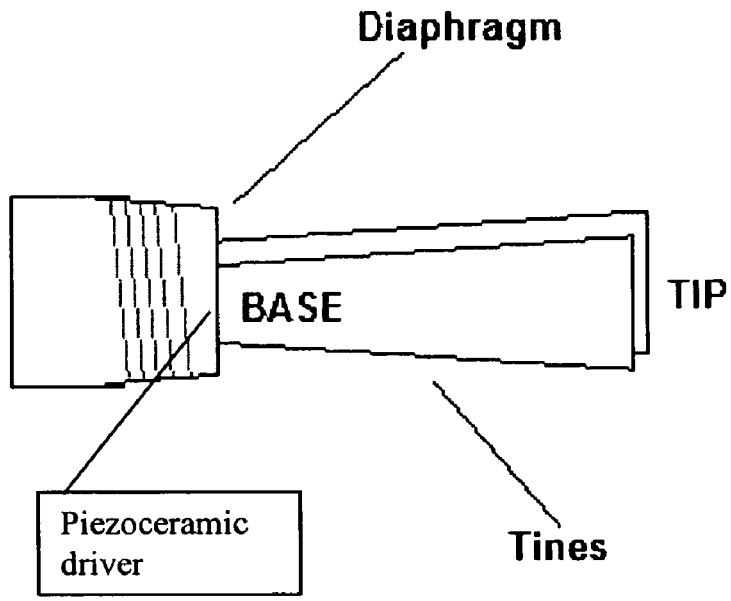
FIG. 2 illustrates the plan view of a commercial tuning fork used to collect data (referred to as fork A).
Figure 3:
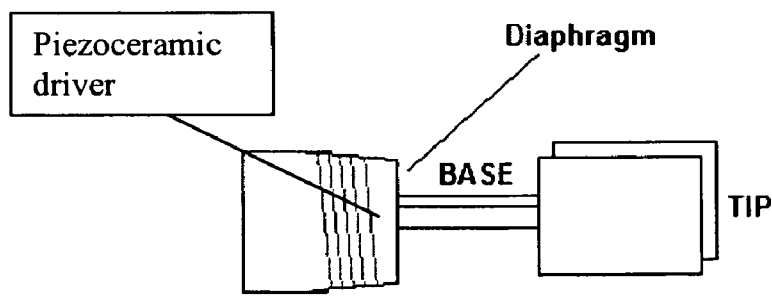
FIG. 3 illustrates the plan view of a commercial tuning fork used to collect data (referred to as fork B).

It has been discovered that the resonance effects of mass loss and scale deposition are a function of position on the tuning fork tine. FIG. 2 illustrates the tines of a commercial tuning fork level sensor (FORK A) used to collect some data that follow. The figure identifies a "diaphragm", "tip" and "base" portion of the tuning fork. FIG. 3 shows a similar plan view of another commercial tuning fork level sensor (FORK B). The tine shape of FORKS A and B are different. As described in this invention, the tine shape has an impact on the sensitivity to measure corrosion. The vibratory excitation for tuning FORKS A and B is achieved with a piezoceramic driver attached to the diaphragm.

Figure 4A:
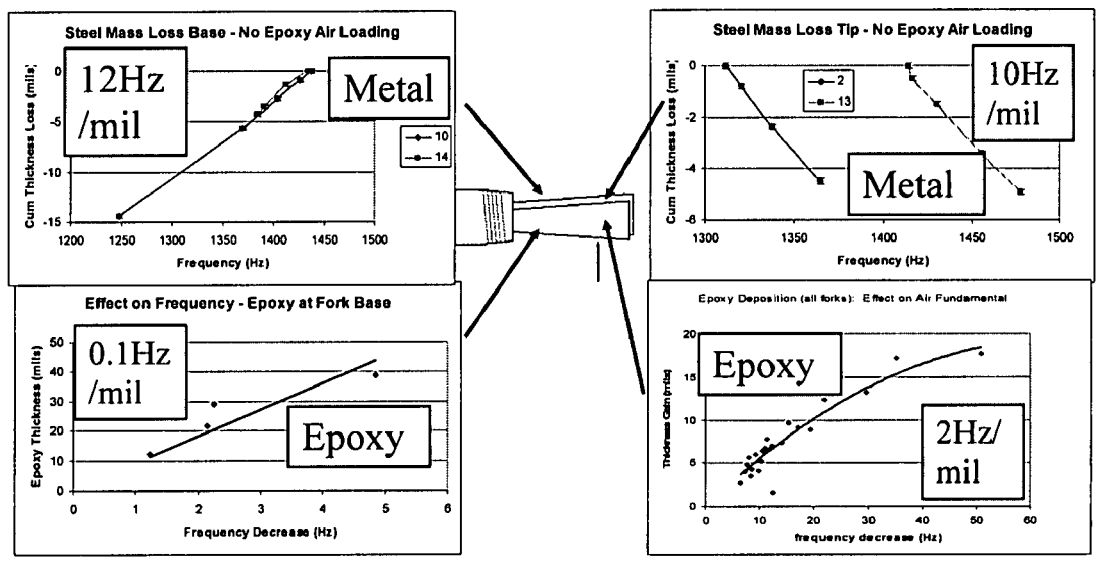
FIG. 4a distinguishes the effect of deposition and mass loss at the tine base from that at the tine tip for fork A.
Figure 4B:
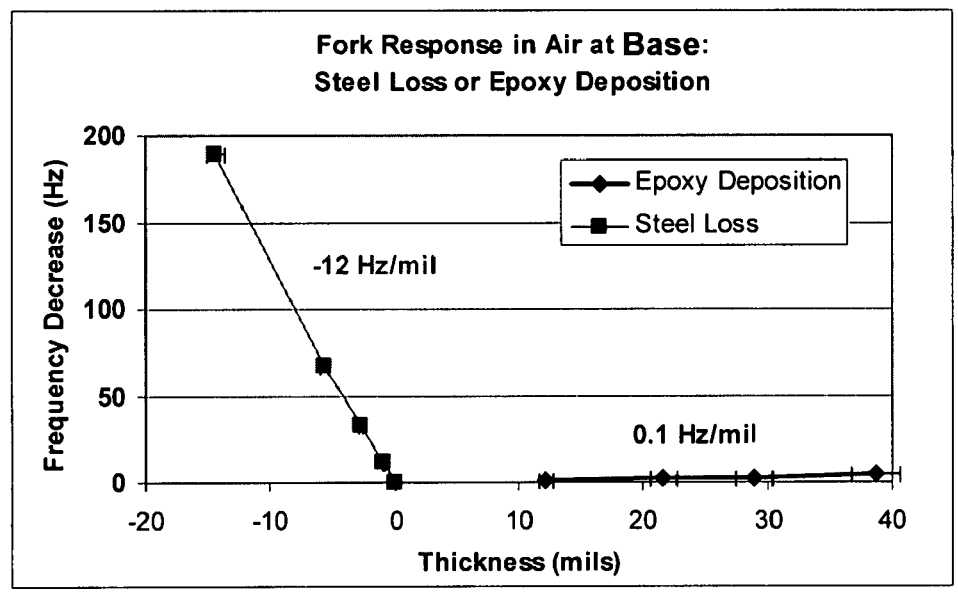
FIG. 4b makes a direct sensitivity comparison to metal loss and deposition at the base of Fork A.

FIGS. 4a and 4b show the effect of deposition, achieved by epoxy addition, and metal mass loss at tine tip and base for FORK A. Mass loss at the tine tip causes an increase in resonance frequency and mass loss at the tine base causes a decrease in the resonance frequency. Deposition at either the tine tip or base causes a decrease in resonance frequency. Additional key observations:
1. At the base, the effect on the resonance change is much more pronounced for metal mass loss than for deposition (difference by approximately a factor of 100). For direct comparison, these parameters are plotted on the same axis in FIG. 4b.
2. At the tine tip, the relative impacts of steel mass loss and deposition differ by only a factor of 5.
3. The data in FIG. 4a of the epoxy deposition at the fork tip were actually collected on four forks of similar construction. Although the four forks used to collect these data are the same model from a single manufacturer, one has a base case resonance frequency approximately 100 Hz lower than the other 3 forks. Notwithstanding this difference, the effect of epoxy deposition on the relative changes in the resonance frequency is predictable and consistent.

Figure 5:
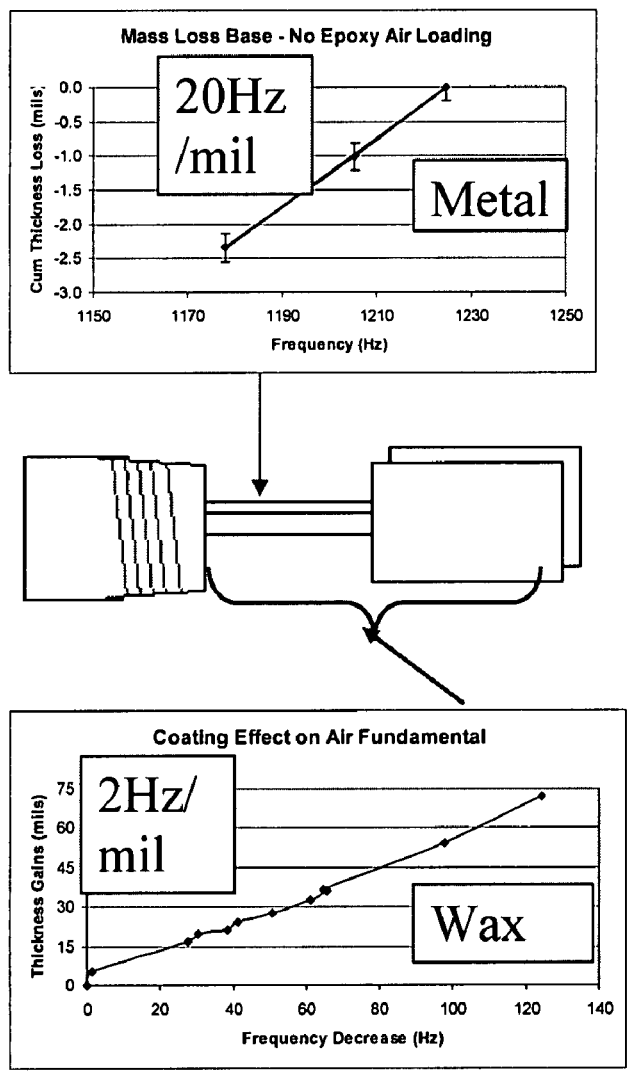
FIG. 5 shows the effect of deposition over the entire fork tine and mass loss at the tine base for fork B.

FIG. 5 shows similar data for FORK B. Although the impact of deposition is similar to the FORK A case, the sensitivity to metal mass loss is approximately 50% greater than FORK A. Table 1 summarizes all of the sensitivities for both forks as measured in air and water.

For some applications, the primary source of deposition will be from the corrosion scale. Although deposition from fouling is possible in several services where these probes may be used, it is typically expected that depositional fouling with high fluid velocity or non-heat transfer conditions will be minimal. For these non-fouling services, one oscillator design approach is to fabricate the tine tip from a corrosive-resistant material (e.g. stainless steel for some services) and fabricate the base from the corrodible material of interest (e.g. carbon steel in some services). Since the diaphragm of the tuning fork now forms the pressure boundary, it should be fabricated from a material that will not fail from corrosion. With this fabrication scenario, metal sulfide, oxide or other scale deposition caused by corrosion will be limited to the base section. Since the tip is configured from a material that will not corrode, there will be no corrosion scale deposits there. Therefore, if the deposition is limited to the by-product of corrosion (in this case iron sulfide), the very limited frequency effects from deposition on the base area (FIGS. 4a/b, 5 and Table 1) will have virtually no effect on the resonance frequency. Therefore, under this case resonance frequency can be used as the indicator for metal mass loss. Rather than using tines of a bimetallic construction, an alternative approach is to apply a suitable protective coating, metallic or non-metallic, to the tine tips.

However, in other services, there may be deposition from sources other than the corrosion product. Some services are subject to deposition from fouling (coking, wax, and/or inorganic salts). In the event of services subject to deposition from fouling, use of the bimetallic fork will not be sufficient to prevent deposition on the non-corrodible element (e.g. fork tip). Therefore, deposition can be expected in some services and will have some impact on the resonance frequency. It is well-known in the prior art that deposition on these non-corrodible elements (often various alloys like stainless steel) can be significantly reduced by electro-polishing methods. In cases where fouling deposition is still problematic, the presence of deposition can be detected by trending Q as shown in FIG. 6a/b. As shown in FIG. 6b, deposition decreases both Q and the resonance frequency. FIG. 6a shows how to estimate the relative frequency decrease corresponding to a measured Q. FIG. 7 also shows that metal mass loss at the base does not decrease Q. These findings form the basis of an algorithm (subsequently described) to estimate metal mass loss in the presence of scale deposition on all fork components.

Figure 13:
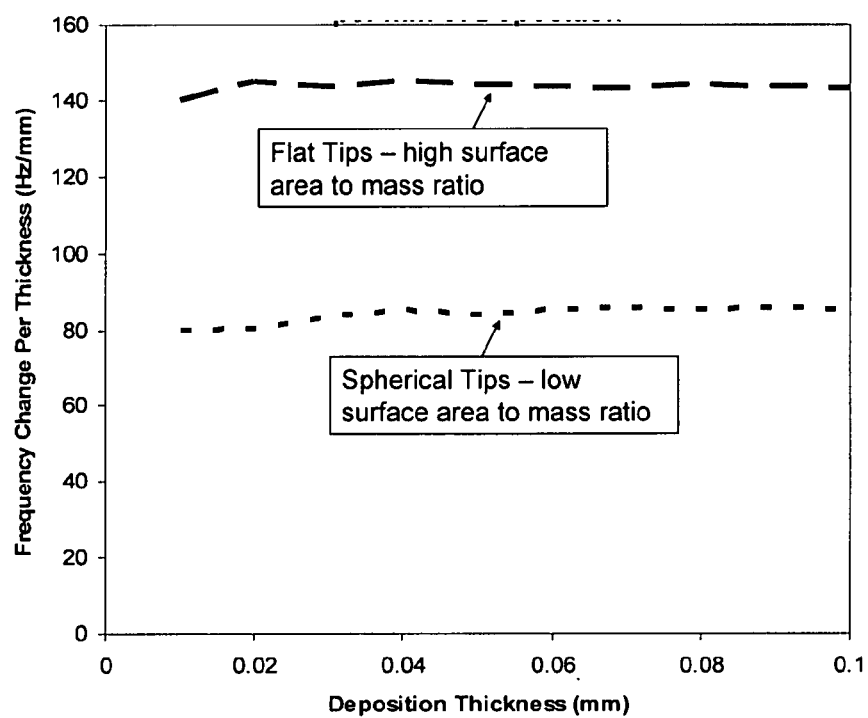
FIG. 13 shows how finite element analysis (FEA) can be used to optimize the paddle shape by minimizing the effect of deposition material.

The data in Table 1 and FIGS. 4/5 demonstrate that the shape of the tines can be used to improve the differentiation of metal mass loss and deposition. Using a ball shape at the tine tip has an additional benefit because a spherical shape minimizes surface area to volume ratio. Minimizing the tip surface area has the desirable effect of minimizing the area for deposition. As shown in FIG. 13, minimizing surface area with the spherical shape results in a reduced frequency decrease per thickness of deposition.

TABLE 1

Summary of Resonance Frequency Response: Fork A and Fork B

| Loading | Air Loading | | Water Loading | |
|---|---|---|---|---|
| Parameter | Fork A | Fork B | Fork A | Fork B |
| Base metal loss (Hz/mil) | 12 | 20 | 9 | 16 |
| Base deposition (Hz/mil) | ~0.1 | <0.1 | ~0.1 | <0.1 |
| Ratio: metal loss to base deposition | ~120 | ~200 | ~90 | ~160 |
| Tip deposition gain (Hz/mil) | 2 (epoxy) | 1.8 (wax) | 3 (epoxy) | 2 (wax) |

Figure 8:
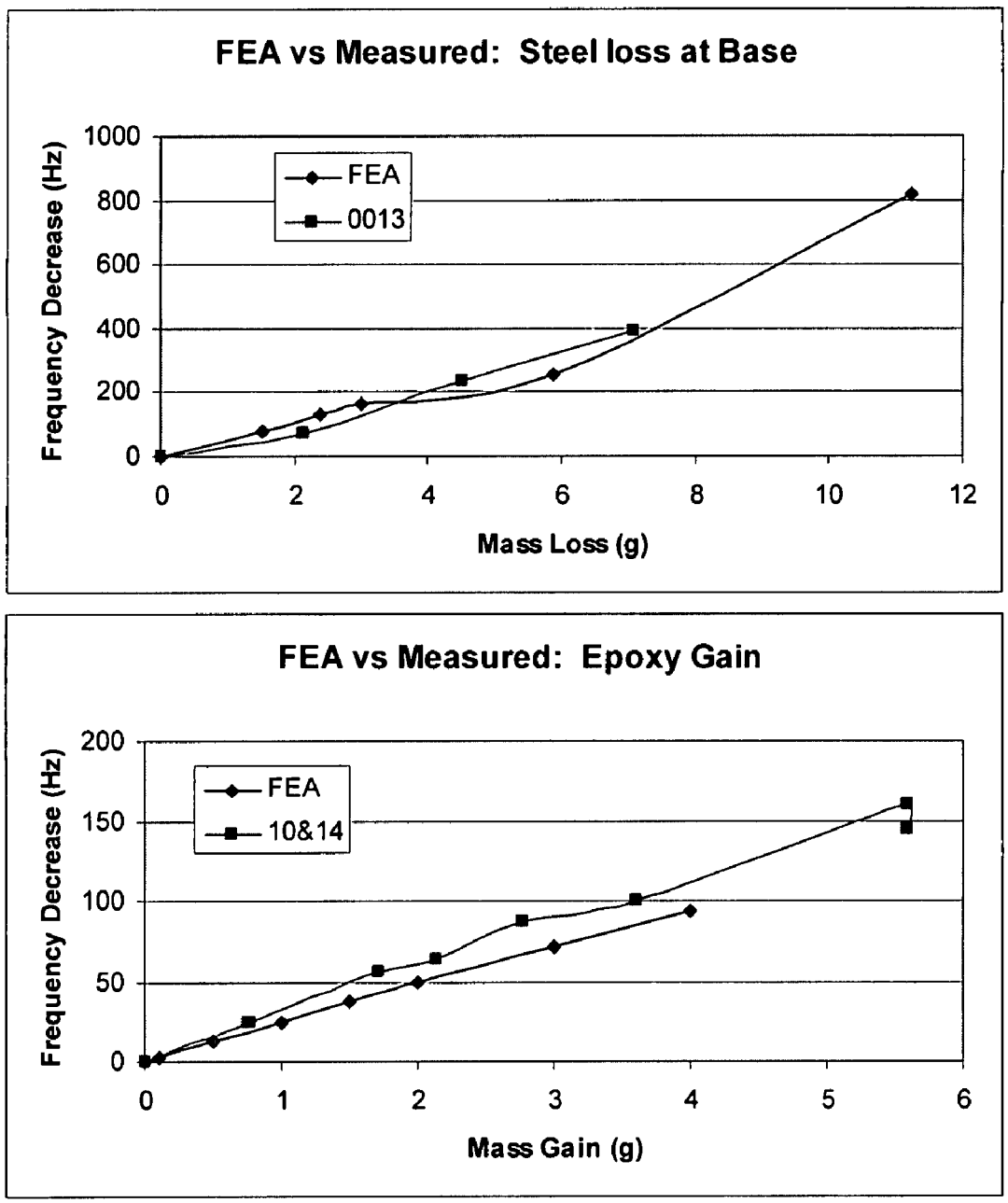
FIG. 8 shows a comparison between the experiment results and finite element analysis.

The present invention includes a component to employ shape optimization. Although shape optimization may be helpful to improve discrimination of mass loss versus scale deposition, there are other potential benefits. For example, it may be desirable to maximize the probe sensitivity near end of probe life. As shown in FIG. 8, this work has demonstrated the viability of using finite element analysis (FEA) to model the fork resonance frequency. FEA correctly models the resonance frequency response to metal mass loss and epoxy deposition. The application of FEA to determine the tine shape can be used to assist in optimizing the tine design for specific applications. Details of FEA can be found in references 1 and 2. Oscillators for the metal loss application may be sized for macro (plant applications) or micro (oscillator lengths on the order of 125 micrometers) scale applications (laboratory testing including high throughput experiments).

Algorithm for the Single Fork Metal Loss Probe

As discussed above, the corrosion/erosion sensor determines metal loss in a corrosive/erosive environment. The measured frequency, f, of the sensor is related to the metal loss. However, the environment may also deposit material on the sensor. This deposition will alter the measured frequency from what it would have been with only corrosion or erosion. Although the corrosion sensor of the instant invention is designed to minimize the impact from deposition, there may be situations where it is necessary to account for deposition. In these situations, the change in frequency attributable to deposition can be determined by the measured value of Q. Q can be related to the change in frequency due to deposition over what it would have been with only metal loss from corrosion or erosion. The measured frequency, f, when corrected for this change in frequency due to deposition, can then be used to determine metal loss due to corrosion or erosion. This procedure is described below.

As previously described, tuning forks of similar design and fabrication will have similar but not identical resonance responses. However, the resonance responses will be sufficiently similar enabling parameter trending on one fork to be predictive of that trend on a similar fork. Although relative values of specific parameters (frequency, Q and amplitude) may vary, trending will be similar. The steps to prepare an algorithm for the metal loss measurement are outlined below. Fork 1, Fork 2, etc. are physically different forks but they are of similar geometric design and fabrication.

The most general case allows for the possibility of both metal mass loss and deposition. However, it is noted that in cases of heavy organic deposition corrosion losses are typically small. In contrast, aqueous applications may have thick depositions that may be a precursor as well as a direct cause of the corrosion. A deposition of amine chlorides is an example that absorbs water and becomes locally corrosive. For hydrocarbon (organic) applications, the primary deposition is the corrosion scale and its impact on the resonance frequency measurement is minimized by the bimetallic fabrication of the tines. Field experience suggests that corrosion product deposition (for example iron sulfide scale) will form rapidly from the outset and then grow very slowly if at all. Although the mechanical oscillator can differentiate between metal loss and deposition, the user should assess the implications for the particular application being served.

1. Construct a tuning fork preferably with tines of bimetallic metallurgy. The metallurgy should be chosen to minimize corrosion at the tine tip area and to be representative of the subject metallurgy at the base area. The metallurgy fork diaphragm should be selected to minimize corrosion. Example materials for the case of refinery streams subject to sulfur corrosion would be stainless steel (non-corrodible) and 5Cr 0.5Mo, respectively for the tine tip and base. This example assumes that the metallurgy of the subject piping is a 5Cr 0.5Mo alloy.
2. Fork 1: Using a format outlined in FIG. 4 or 5, measure the fundamental resonance frequency and Q as a function of deposition on the tine near the base. The deposition material should have mechanical stiffness properties and density similar to that of the expected depositions. These measurements should be made in a medium of representative viscosity of the actual test fluid.
3. Fork 1: Using a format outlined in FIG. 6, measure the fundamental resonance frequency and Q as a function of deposition over the entire tine and diaphragm. These measurements should be made in a medium of representative density, temperature, and viscosity of the actual test fluid.
4. Fork 1: Using a format outlined in FIG. 4 or 5, measure the fundamental resonance frequency and Q as a function of metal mass loss at the base of the tines with all depositions removed.
5. These measurements outlined in steps 2-4 should continue on Fork 1 in discrete mass loss increments (at the base of the tine) to fork failure. For each increment of metal loss, the application of deposition (step 3) is repeated. By running this calibration procedure to failure of the fork, it provides information to enable replacement prior to failure when installed in the service fluid. By monitoring the resonance frequency and Q, the operator will know when the tuning fork has reached a predefined replacement thickness.
6. Test cases, shown in FIG. 7, have demonstrated no decrease in Q for tine shapes shown in FIGS. 2 and 3 of metal mass loss (without scale deposition). For these fork designs, the system Q (fork+deposition) is controlled by the deposition rather than any modest increase in the fork Q associated with metal mass loss.

Figure 10:
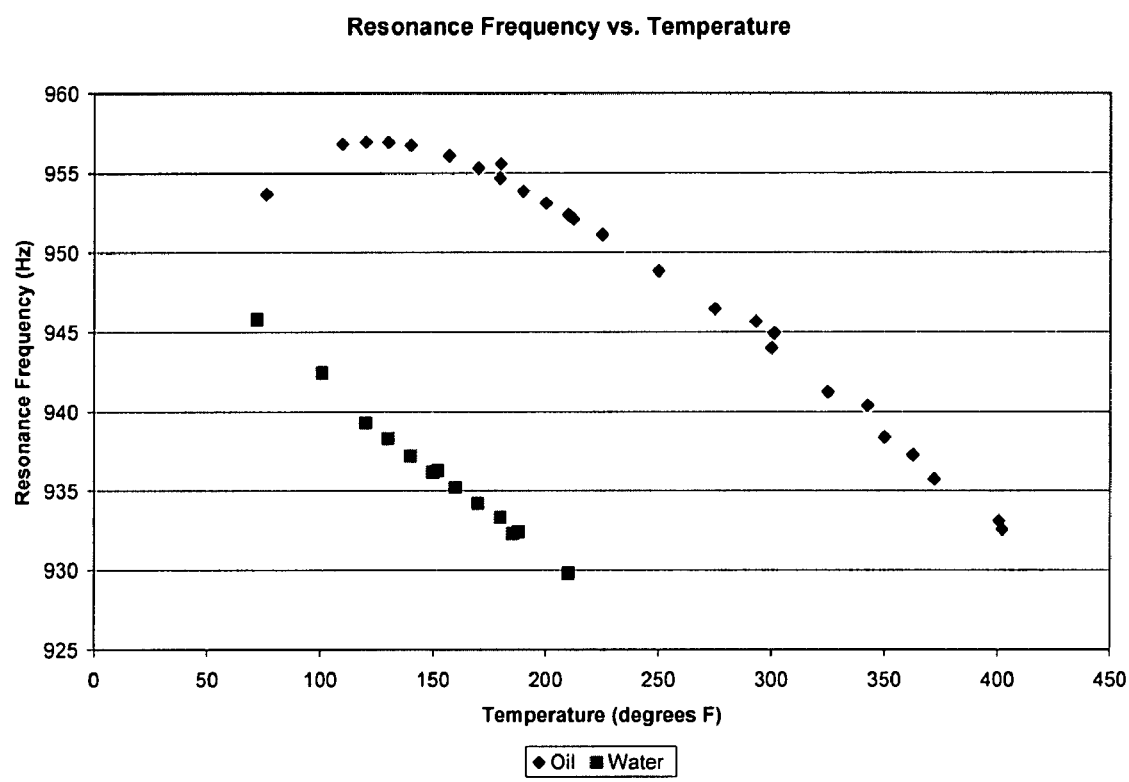
FIG. 10 shows the effect of temperature on resonance frequency and Q of another tuning fork, Fork C.

The following functions are defined:
$\Delta f$ deposition=$|G(Q)|$ (FIG. 6)
Metal loss=$H(\Delta f$ metal loss) (FIG. 5)
$\Delta f$ measured=$\Delta f$ corrosion+$\Delta f$ deposition
From the above equations, $\Delta f$ metal loss=$\{\Delta f$ measured−$G(Q)|\}$
▶Metal loss=$H(\{\Delta f$ measured−$|G(Q)|\})$ 7. FIG. 10 provides an example relating an effect of fluid temperature on the resonance parameters: frequency and Q. The change in resonance parameters is caused by the combined impact of temperature and the corresponding impact on density and viscosity. For the intended refining and petrochemical applications, temperature variations are likely limited to a range of ±10° F. Because the high temperature already provides a low viscosity environment, it is unlikely that the service fluid viscosity change caused by small temperature variations will have a significant impact. However, compensation for temperature is readily incorporated into the measurement process. By making a concurrent temperature measurement, a tabulation of adjustment factors can be provided to account for the combined effects on resonance frequency and Q caused by the various impacts of temperature.

Example on using the above algorithm. This example demonstrates a boundary condition case: a situation where deposition after calibration with no new metal loss can be distinguished as deposition rather than metal loss. As outlined in Step 2 above, FORK B shown in FIG. 5 had measurements of resonance frequency (without deposition) as a function of metal mass removal. FIG. 6b shows the frequency response as a function of wax mass deposition for the final metal mass loss condition of FIG. 5.

A summary of the FORK B parameters with no mass loss are summarized in Table 2:

TABLE 2

FORK B Parameters with No Metal Mass Loss

| FORK B Condition | Resonance Frequency (Hz) | Q |
|---|---|---|
| No deposition and no mass loss (Resonance frequency shown in FIG. 5a) | 1225 | 1039 |
| With 1.19 g deposition/no mass loss (not shown in figures) | 1192 | 976 |
| Change caused by deposition of 1.19 g | 33 Hz (decrease) | 63 (decrease) |

In FIG. 5, with a metal mass loss causing 2.3 mils thickness reduction (total thickness loss of 4.6 mils); the resonance frequency with no deposition is 1178 Hz. This metal thickness corresponds to a loss of 0.25 g. In this example, the intent is to use the Table 2 calibration to show how deposition can be correctly assessed. For this example, it is desired to know the metal loss at the time when the sensor records a Q of 976. Table 3 shows the results of applying a measured Q of 976 to account for an unknown amount of deposition. In an actual case, it is likely that interpolation would be required if the measured Q did not exactly correspond to a Q that was tested during the calibration process.

above equations apply, but should be modified as follows to account for the metal mass loss:

$$\Delta f \text{deposition} = |G(Q, \Delta \text{mass})|$$

The measurements outlined above provides a template to assess the corrosion of another fork (FORK 2) in the actual test fluid. If the test conditions are corrosive without any deposition, then the measure of resonance frequency estab-

TABLE 3

Interpolation of FIGS. 6a/b for FORK B with a Metal Mass Loss of 0.25 g

| A | B | C | D | E |
|---|---|---|---|---|
| Measured Q for an unknown amount of metal loss and an unknown amount of deposition Q = 976 | Resonance frequency resulting from metal mass loss of 2.3 mil (from FIG. 5a) 1225 − 47 = 1178 Hz | Estimated deposition (g) for Q = 976 (from FIG. 6b) Deposition ~1.31 g | Measured frequency Shift (Hz) from deposition and metal loss (FIG. 6a, Q = 976) 1178 − 1143 = 35 Hz | Apply Table 2 frequency shift due the to deposition corresponding to Q = 976 (FIG. 6a) to the measured frequency (col D) 33 + 1143 = 1176 Hz |
| The starting metal is 0.25 g corresponding to 2.3 mil of thickness decrease. The measured Q is to estimate deposition | This frequency is the target in the absence of either deposition and no additional metal loss | Not explicitly used in the calculation process | 1178 is the starting frequency from column B | Applying the above correction underestimates the target frequency of column B by 2 Hz |

The above example is used to demonstrate that the frequency shift due to wax deposition can be accounted for using the application of Q. In Table 3, applying the Q established for the no metal mass condition (from Table 2) to the case with metal mass loss of 2.3 mils results in an estimated resonance frequency without deposition of 1176 Hz. As observed in FIG. 5 and Table 3, the actual resonance frequency for 2.3 mils of metal thickness loss with no deposition is 1178 Hz. If this entire 2 Hz frequency discrepancy is attributed to metal mass loss, the overestimated metal mass loss=0.1 mil (=2 Hz/(20 Hz/mil). Some error is attributable to the interpolation of FIG. 6 to find a Q value corresponding to the calibration condition. In practice, the calibration will consist of a series of measured depositions and corresponding Qs. This approach will reduce interpolation error. In Table 3, the estimate of wax deposition (1.31 g) using Q is slightly greater than the actual deposition of 1.19 g. However, the error in metal mass loss is comparatively smaller because of the relative insensitivity of the tine shape to deposition versus metal mass loss. This example demonstrates the viability of measuring metal loss in the presence of deposition covering the entire tines.

For the generalized case with larger amounts of metal mass loss, it is possible that the functional relationship between Q and deposition may be more complex than in the previous example. Although not yet observed, there may be cases where metal loss may also result in a decrease of its initial level as a function of metal mass loss (without scale deposition). It is recognized that knowing the values of Q, amplitude, and resonance frequency may not always uniquely map into a mass loss and deposition. However, by continually recording these parameters, the metal mass loss can be tracked. Knowing the metal mass loss does provide a unique mapping using steps 2-4 to assess deposition. It is not only necessary to know the values of amplitude, Q, and frequency but also the path taken to get to those values. It should also be anticipated that there may be applications which result in a spalling or erosion of the corrosion scale. That condition would be identifiable by a rapid increase in resonance frequency accompanied by a Q increase. Mathematically, the lished in step 2 is sufficient to estimate the corrosion using Fork 2. The corrosion using Fork 2 is predicted by using the "mils/Hz" established during step 2. If the functional relationship between metal mass loss and resonance frequency is non-linear, then this rate changes as a function of metal loss. It has been observed that this functional relationship will be similar for similarly designed forks (as example Fork 1 and Fork 2 in FIG. 1b) but possibly offset by a constant. Although testing has shown some device to device variability regarding the absolute resonance parameters, for a given commercial design the resonance parameters are sufficiently similar to translate or infer properties measured on Fork 1 to subsequent fork oscillators.

The condition of deposition and metal mass loss is recognized by a decrease in Q accompanied by a decrease in resonance frequency. By continually recording resonance frequency and Q, it is possible to map the test conditions to the reference conditions established in steps 2-4.

Corrosion Sensor Orientation in the Process Stream

Figure 9:
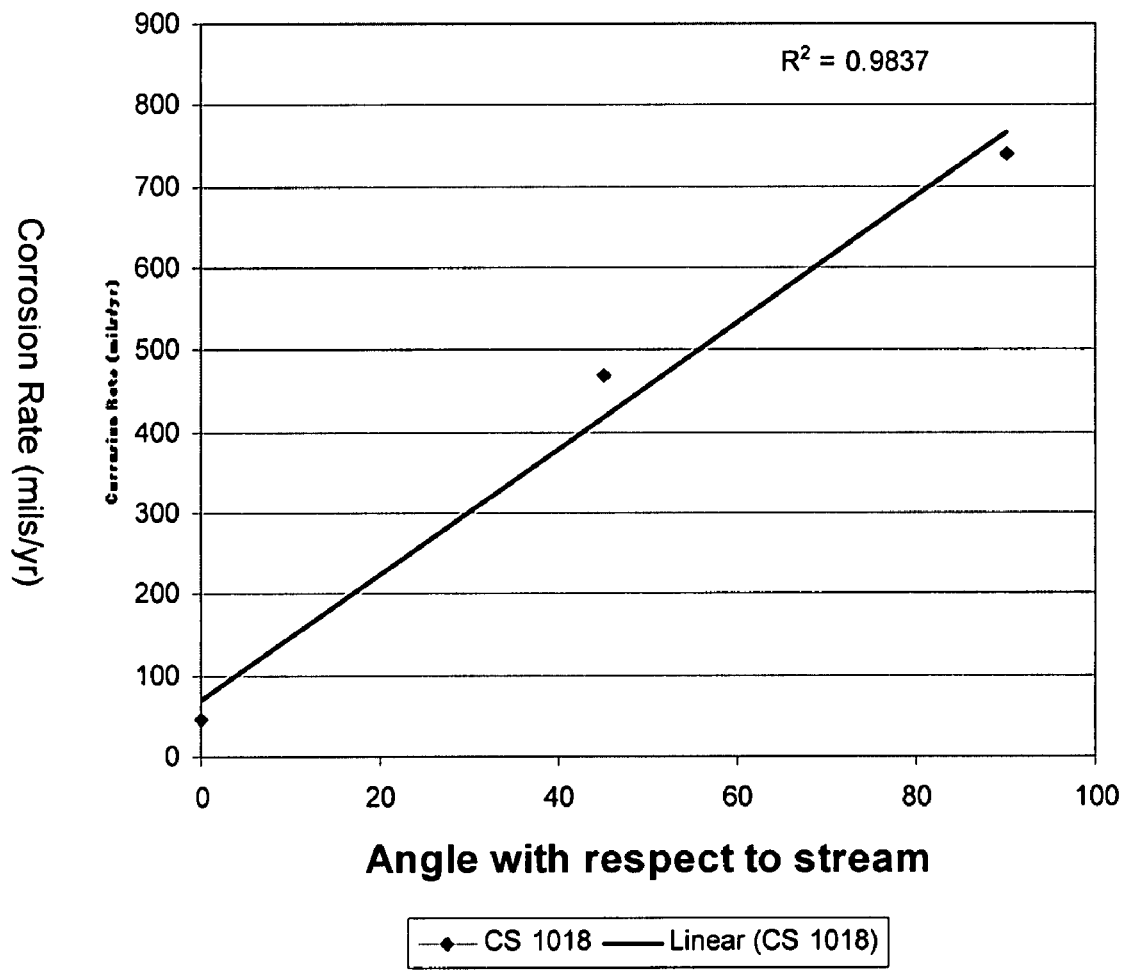
FIG. 9 shows the corrosion rate as a function of impact angle.

As shown in FIGS. 2 and 3, some tine shapes are not completely symmetric. Therefore, the orientation of the tines with respect to the process flow has an important consequence. In the extreme cases, the orientation can maximize or minimize the flow impact on the tine surface area. As shown in FIG. 9, the metal loss is greatest when the orientation of the tine is such that the maximum amount of surface area is perpendicular to the flow. The metal loss is minimized when the least amount of surface area is perpendicular to the flow. This phenomenon can be used so that the metal loss sensor can be adjusted to simulate various geometric discontinuities typically found in process piping and vessels.

Computation of Metal Loss Rate

A procedure has been devised for measuring the amount of metal loss. Moreover, the quantity of metal loss can be determined independently from fouling and scale deposition. For the case of constant stream operating conditions, the metal loss rate sometimes referred to as the corrosion rate, can be readily calculated from the information already provided.

The calculation divides the amount of incremental metal loss by the corresponding time the metal loss sensor has been exposed to the subject process stream. Calculations can be made over the life of the sensor to indicate a "long term" corrosion rate, or they can be made between discrete readings to give "short term" rates during a particular exposure period. To minimize the effects of noise introduced by small process variations, a preferred approach for computing the corrosion rate is to calculate a statistically regressed slope on the measured resonance frequency as function of time.

Applications of the Metal Loss Sensor

There are two primary application of the metal loss sensor. One application is to assess the amount of metal remaining at the pressure boundary (e.g. pipe, vessel, etc.). Typically, it is desired to know the thinnest wall thickness at the pressure boundary. This information provides the operator of the process unit with information that it is necessary to take suitable actions to prevent product leaks from the pressure boundary. This end point of the pressure boundary may be referred to as the retirement limit. Using the calibration procedure described in this invention, the amount of quantifiable metal loss from the metal loss oscillator can be used as an indicator of the metal loss at the pressure boundary. A second application is to use the metal loss rate as a predictor regarding when the pressure boundary will reach its retirement limit and can additionally prompt direct inspections of the pressure boundary. For both of these applications, the operator can conservatively estimate the maximum metal loss or metal loss rate by selecting a sensor orientation that maximizes the sensor area that is perpendicular to the flow of the process stream. In addition to measuring the retirement limit of the pressure boundary, it is possible to define a retirement limit for the metal loss sensor itself.

An alternative to measuring the maximum metal loss or the maximum metal loss rate is to measure both the minimum and maximum rates. This approach will provide the operator with information regarding the expected extremes of metal loss at the service pressure boundary as a function of geometry. As an example, the operator can have information regarding metal loss in low turbulence straight pipe sections or at pipe elbows where turbulence would be expected to be higher. Typically corrosion and erosion are higher at pipe locations with increased turbulence. This application can be achieved by using two metal loss sensors with different geometries. The shape geometries would be selected to optimize hydrodynamics to provide a suitable range of anticipated metal loss rates within the subject service. This approach has an advantage over traditional corrosion probes that requires selection of the correct physical placement in the subject service to achieve a suitable range of metal loss hydrodynamics.

Figure 11:
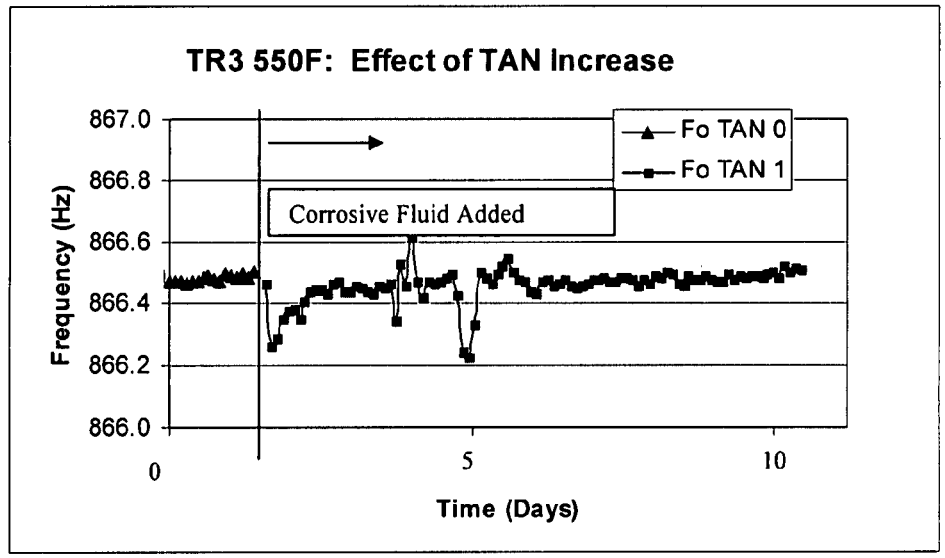
FIG. 11 shows a case where the probe resonance frequency remained constant in a corroding environment with concurrent carbonaceous deposition.
Figure 12:
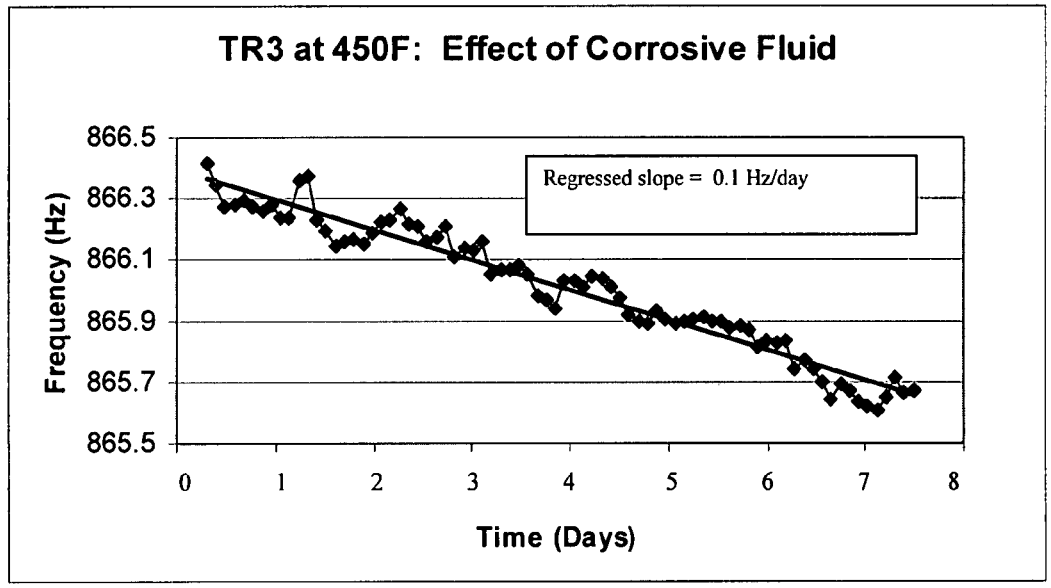
FIG. 12 show the same device of FIG. 11 but in an environment where corrosive fluid has an impact on resonance frequency.

FIG. 11 shows an example where the corrosive fluid is injected into an autoclave operating at 550° F. Although the ambient temperature fluid causes a short term impact on the resonance frequency, there is no long-term corresponding impact on the resonance frequency. In this case, the resonator is a tuning fork device with non-corrodible tine tips and a corrodible tine base. Although a frequency decrease would have been anticipated, none was observed. When the tuning fork was removed from the autoclave, it was observed that a carbonaceous deposit had formed covering the corrodible tine base area. After removing the carbonaceous deposition, pre- and post exposure mass measurements confirmed that there was no steel mass loss during the corrosive exposure. The carbonaceous deposition protected the corrodible tine base from any mass loss. The tuning fork device behaved as designed: no frequency change from the deposition. In contrast, FIG. 12 shows the result using the same tuning fork in the same autoclave but where the temperature has been reduced to 450° F. and a different corrosive fluid. Under these reduced temperature conditions, the propensity for coking is reduced. FIG. 12 demonstrates the frequency decrease associated with the measured mass decrease from the tuning fork tines.

REFERENCES

1. Concepts and Applications of Finite Element Analysis, Robert D. Cook, David S. Malkus Michael E. Plesha. Fourth Edition, Wiley & Sons Publisher
2. The Finite Element Method. Vol. 1. Basic Formulations and Linear Problems. London: McGraw-Hill, 1989. 648 p. Vol. 2. Solid and fluid mechanics: Dynamics and Non-linearity. London: McGraw-Hill, 1991. 807 p. [School of Engineering, University of Wales. Swansea, Wales] 5th edition published in 2000
3. Shock and Vibration Handbook, Third Edition, McGraw-Hill Book Company
4. Mechanical Vibration and Shock Measurements, Jens Trampe Broch, Bruel & Kjaer Equipment Company, K. Larsen & Son, Seborg, Denmark.

What is claimed is:

1. A mechanical oscillator metal loss sensor for use in a corrosive or erosive environment that results in metal loss comprising
    a) a means for mechanical excitation
    b) a mechanical oscillator with two regions that corrode differently, wherein said mechanical oscillator has a tip region not affected by the corrosion or erosion environment and a base region that is affected by the environment where the regions determine the resonance parameters, and wherein said mechanical oscillator has a resonant frequency, f, and a quality factor, Q, so that said metal loss results in a resonant frequency decrease of the mechanical oscillator.

2. The mechanical oscillator metal loss sensor of claim 1 wherein the regions are positioned to determine the resonance parameters.

3. The mechanical oscillator metal loss sensor of claim 1 wherein the regions are shaped to determine the resonance parameters.

4. The mechanical oscillator metal loss sensor of claim 1 wherein said mechanical oscillator is in the shape of a tuning fork.

5. The mechanical oscillator metal loss sensor of claim 4 wherein said tuning fork has two tines.

6. The mechanical oscillator metal loss sensor of claim 4 wherein said mechanical oscillator has a tip that is spherical and a tine base that is a 7. The mechanical oscillator of claim 6 wherein said fork is a bimetallic fork. rod.

8. The mechanical oscillator metal loss sensor of claim 1 wherein said corrosive environment is a gas or a liquid.

9. The mechanical oscillator of claim 1 wherein the corrosion or erosion environment changes the system stiffness to change in a way that causes a net resonance frequency decrease.

10. The mechanical oscillator metal loss sensor of claim 1 wherein said mechanical oscillator is driven by mechanical excitation of the environment in which the mechanical oscillator is placed.

11. The mechanical oscillator metal loss sensor of claim 10 wherein said mechanical excitation is due to fluid flow in said environment.

12. The mechanical oscillator metal loss sensor of claim 11 wherein the shape of the mechanical oscillator maximizes metal loss response and minimizes deposition response to the resonance parameters.

13. The mechanical oscillator of claim 12 wherein corrosion to deposition has a ratio of greater than 50.

14. The mechanical oscillator metal loss sensor of claim 1 wherein said mechanical oscillator is excited by external piezoceramic, electromagnetic or magnetostrictive means.

15. The mechanical oscillator metal loss of claim 1 wherein said mechanical oscillator has the shape of a rod.

16. The mechanical oscillator metal loss sensor of claim 1 further comprising a second mechanical oscillator that is not affected by the corrosivity of the environment.

17. The mechanical oscillator metal loss sensor of claim 1 wherein said environment produces deposition on said oscillator.

18. The mechanical oscillator of claim 17 wherein said tip region is corrosion resistant and electro-polished.

19. The mechanical oscillator metal loss sensor of claim 1 where the position of the two regions minimizes deposition response to the resonance parameters.

20. The mechanical oscillator of claim 19 wherein corrosion to deposition has a ratio of greater than 100.

21. The mechanical oscillator of claim 1 wherein said base region has mass loss due to corrosion.

22. The mechanical oscillator of claim 1 wherein said tip region is corrosion resistant.

23. The mechanical oscillator of claim 22 wherein said corrosion resistant tip region is achieved by application of a coating.

24. The mechanical oscillator of claim 1 wherein said tip region has deposition gain.

25. The mechanical oscillator metal loss sensor of claim 1 further comprising a means for measuring temperature and for compensating the frequency decrease of the mechanical oscillator for changes in temperature, density, and viscosity based upon the measured temperature.

26. The mechanical oscillator metal loss sensor of claim 1 further including a second mechanical oscillator.

27. The mechanical oscillator metal loss sensor of claim 26 wherein said mechanical oscillator and said second mechanical oscillator are in the shape of tuning forks.

28. The mechanical oscillator metal loss sensor of claim 27 wherein said second mechanical oscillator is non-corrodible.

29. A method to determine the corrosion or erosion rate for fluid flow in a corrosive or erosive environment using the mechanical oscillator metal loss sensor of claim 1 comprising:
   a) exciting the mechanical oscillator of said mechanical oscillator metal loss sensor;
   b) measuring the resonant frequency f and Quality factor Q of the mechanical oscillator;
   c) determining a resonant frequency decrease in the mechanical oscillator; and
   d) determining said rate by the frequency decrease measurement due to a metal loss.

30. The method of claim 29 where the corrosion or erosive rate is determined by making successive measurements over time to enable the computation of a statistical regression of the mechanical oscillator resonance parameters over the time period.

31. The method of claim 30 wherein said determination of said corrosive or erosive rate includes for deposition.

32. The method of claim 30 wherein said corrosive or erosive rate is determined by measuring Q, measuring f, determining the change in f due to Q, correcting f for the change in f due to Q, and determining mass loss from the corrected f.

33. The method of claim 30 wherein said mechanical oscillator is in the shape of a tuning fork and wherein the shape of the tuning fork tines is optimized for a specific application by employing finite element analysis.

34. The method of claim 29 wherein said corrosive or erosive environment includes a deposition environment.

35. The method of claim 29 wherein said mechanical oscillator metal loss sensor is oriented so that maximum metal loss at high turbulence flow can be determined.

36. The method of claim 35 wherein said mechanical oscillator metal loss sensor is not located at the high turbulence fluid flow.

37. The method of claim 29 wherein the excitation of said mechanical oscillator is only performed when it is desired to interrogate the sensor.

* * * * *